(12) United States Patent
Meier et al.

(10) Patent No.: US 8,998,103 B2
(45) Date of Patent: Apr. 7, 2015

(54) FRAGRANCE DISPENSING SYSTEM WITH ACTIVATION INDICATOR AND/OR CONSUMPTION INDICATOR

(75) Inventors: Frank Meier, Dusseldorf (DE); Matthias Sunder, Dusseldorf (DE); Matthew Freeborn, Scottsdale, AZ (US)

(73) Assignee: Henkel AG & Co. KGaA, Duesseldorf (DE)

( * ) Notice: Subject to any disclaimer, the term of this patent is extended or adjusted under 35 U.S.C. 154(b) by 265 days.

(21) Appl. No.: 13/439,986

(22) Filed: Apr. 5, 2012

(65) Prior Publication Data
US 2012/0193443 A1   Aug. 2, 2012

Related U.S. Application Data

(63) Continuation of application No. PCT/EP2010/056137, filed on May 6, 2010.

(30) Foreign Application Priority Data

Oct. 8, 2009   (DE) .......................... 10 2009 045 482

(51) Int. Cl.
*A61L 9/04*   (2006.01)
*A61L 9/12*   (2006.01)

(52) U.S. Cl.
CPC ...................................... *A61L 9/127* (2013.01)

(58) Field of Classification Search
CPC ........................................................ A61L 9/127
USPC ........................................ 239/34–60; 428/905
See application file for complete search history.

(56) References Cited

U.S. PATENT DOCUMENTS

| 4,419,326 A * | 12/1983 | Santini .............................. 422/4 |
| 4,874,129 A * | 10/1989 | DiSapio et al. ................. 239/36 |
| 6,435,423 B2 * | 8/2002 | Hurry et al. ..................... 239/34 |
| 7,252,244 B2 * | 8/2007 | Martens, III .................... 239/44 |
| 2008/0251599 A1 * | 10/2008 | Ward et al. ...................... 239/44 |

FOREIGN PATENT DOCUMENTS

| EP | 0309173 A2 | 3/1989 |
| EP | 0462605 A2 | 12/1991 |
| WO | WO 2004/006968 A1 | 1/2004 |

* cited by examiner

*Primary Examiner* — Len Tran
*Assistant Examiner* — Joel Zhou
(74) *Attorney, Agent, or Firm* — P. Scott Smith

(57) ABSTRACT

A fragrance-dispensing system comprises a wick and diffuser, wherein the diffuser surface in contact with surrounding air is larger than the wick surface in contact with the air, a container for receiving the wick, and a fragrance preparation in the container, wherein the fragrance is transported by the wick to the diffuser by capillary action. At least sections of the diffuser include a color-changing agent that interacts with at least one substance present in the fragrance such that a color change is produced on and/or in the diffuser section when the substance comes into contact with the color changing agent.

20 Claims, 1 Drawing Sheet

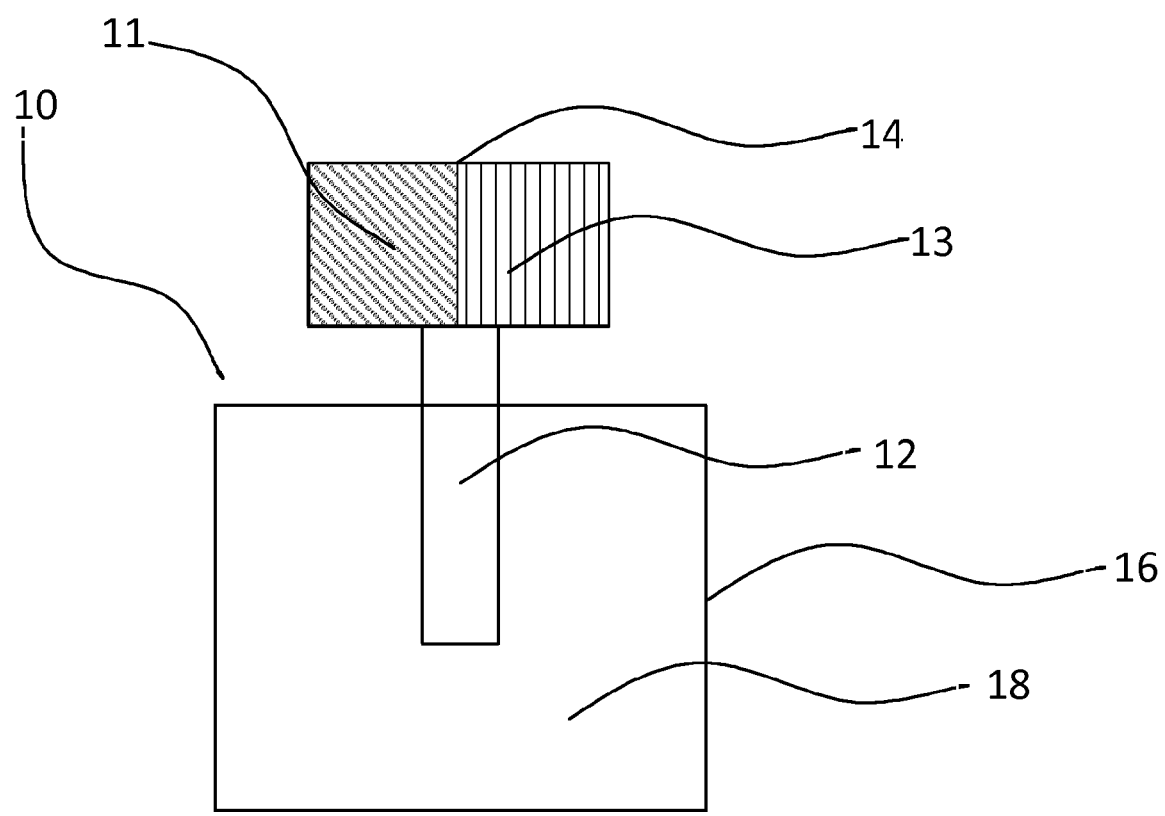

FRAGRANCE DISPENSING SYSTEM WITH ACTIVATION INDICATOR AND/OR CONSUMPTION INDICATOR

CROSS-REFERENCE TO RELATED APPLICATIONS

This application is a continuation of PCT Application Serial No. PCT/EP2010/056137, filed on May 6, 2010, which claims priority under 35 U.S.C. §119 to 10 2009 045 482.9 (DE) filed on Oct. 8, 2009. The disclosures PCT/EP2010/056137 and DE 10 2009 045 482.9 are hereby incorporated by reference in their entirety.

FIELD OF THE INVENTION

The present invention generally relates to a diffusion-driven fragrance-dispensing system having an activation and/or consumption indicator.

BACKGROUND OF THE INVENTION

Diffusion driven fragrance-dispensing systems are well known in the prior art. Systems based on a wick and a container filled with a liquid, fragrance-containing preparation are particularly well known, in which the wick is inserted into the container, and the preparation, as a result of the capillary forces of the wick, is carried against gravity to the surface of the wick, from where the thus-transported fragrance is discharged into the surroundings, normally by evaporation.

A disadvantage of such systems is that the consumer cannot determine whether the system functions correctly after its initial activation—that is discharges as intended into the surroundings—and/or when the system is used up.

Accordingly, the object of the invention is to provide a fragrance-dispensing system that displays to the consumer in an easy way that the fragrance-dispensing system has been correctly activated and/or that the fragrance dispensing system is used up. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

This object is achieved by a fragrance-dispensing system comprising: (a) at least one diffuser having a surface in contact with the surrounding air; (b) a color change agent present in or on at least a section of said diffuser; (c) a wick having a surface area at least partly exposed to said surrounding air, said wick in contact with said diffuser; (d) a container for receiving said wick; and (e) a fragrance preparation in said container and in contact with said wick, said preparation comprising at least one reactive substance capable of reacting with said color change agent; and wherein (i) said fragrance preparation is transported by means of capillary action against the force of gravity from said container through said wick to said diffuser; (ii) said surface of said diffuser in contact with said surrounding air is greater than said surface of said wick exposed to said surrounding air; and (iii) contact of said reactive substance with said color change agent causes a color change to, and/or in, said diffuser section.

BRIEF DESCRIPTION OF THE DRAWINGS

FIG. 1 is a general diagram of an embodiment a system of the invention.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The fragrance-dispensing system 10 in accordance with the present invention includes a wick 12 and at least one diffuser 14 having at least two groups of lamellae 11, 13, wherein the surface area of the diffuser that is in contact with surrounding air is greater than the surface area of the wick that is in contact with the surrounding air. In this way the diffuser causes an increase in the surface area, over which fragrance is dispensed to the surroundings.

The fragrance-dispensing system 10 according to the invention moreover includes a container 16 for receiving the wick 12, as well as a fragrance preparation 18 that is stored in the container, wherein the fragrance preparation is taken up by means of capillary action against the force of gravity into the wick present in the container and transported through the wick to the diffuser. The diffuser 14 and its at least two groups of lamellae are preferably located on the end of the especially stalk-shaped or cylindrical wick facing away from the container.

The diffuser is provided, at least in part, with a color change agent that interacts with at least one substance of the fragrance preparation, such that the substance on contact with the color change agent causes a color change to and/or in the diffuser section.

The wick and/or the diffuser is/are preferably made of a synthetic material and/or a fibrous material of vegetal origin, especially a cellulose-based material. It is of course possible that the wick and the diffuser are produced from the same or different materials.

More advantageously, the diffuser has an essentially circular base in top view, such that the distance between the wick that is connected especially in the center of the circular base with the diffuser, and the external edge of the diffuser is essentially constant. This results in essentially similar diffusion path lengths and times across the base.

In order to produce a higher release of fragrance, it is advantageous that the ratio of the surface of the diffuser in contact with the surrounding air and the surface of the wick in contact with the surrounding air is between 1000:1 and 1.25:1, preferably between 125:1 and 2.5:1.

The diffuser is preferably formed from a plurality of essentially similar lamella, wherein one end of the lamella is fixed in or on the wick. However, according to an advantageous further development of the invention, it is also conceivable that the diffuser is formed from at least two groups of various lamellas that differ from one another.

The number of lamella is in particular at least 6, preferably at least 50, particularly preferably at least 100.

In another particularly advantageous development of the invention, the lamellae each have a surface, consisting of upper and lower sides of a lamella, from 0.5-100 $cm^2$, preferably from 1-75 $cm^2$, and particularly preferably from 2-50 $cm^2$.

It is also possible for the lamellae to be arranged helically (acyclically) or whorled (cyclically) on the wick axis.

The angle between two neighboring lamellae is preferably between 3°-140°, and more preferably between 4°-137.5°.

In another development of the invention, the diffuser formed from the lamellae may have at least one, preferably two, particularly preferably three planes of symmetry.

It is particularly advantageous for the color change agent to be selected from the group of the solvatochromic dyes.

Moreover, it is advantageous to select a color change agent that reacts to the presence of especially non-toxic metal ions, preferably Ca, Mg, Al, Zn and/or Fe.

In another, preferred embodiment of the invention, the color change agent is colorless before contacting the appropriate reactive substance that initiates the color change.

According to another development of the invention, it is also conceivable that the wick and the diffuser are each provided with color change agents that differ from one another.

It is further preferred that a first group of lamellae having a first color change agent and at least a second group of lamellae having a second color change agent are provided. In particular, it is also conceivable here, that the first color change agent and the second color change agent show a color change with the same or different substances present in the fragrance preparation.

The color change substance can be applied onto the wick and/or the diffuser by methods from the prior art that are known to the person skilled in the art, for example by spraying or dipping.

| Color change agent (wick/diffuser) | Color change initiator in fragrance preparation |
|---|---|
| Solvatochromic Colorant | Polar/non-polar solvent (water/ethanol) |
| Eriochrom black T (ERIO T) | Metal ion |
| Murexid | Metal ion |
| Metal phthalein | Metal ion |
| Pyrocatechol violet | Metal ion |
| 1-(2-Pyridylazo)-2-naphthol (PAN) | Metal ion |
| 1-(2-Pyridylazo)-2-resorcinol (PAR) | Metal ion |
| Calconcarboxylic acid (CC) | Metal ion |
| Xylene orange | Metal ion |

According to another embodiment of the invention, the color change agent is ERIO T that forms a red complex with magnesium ions, ERIO T being blue in the absence of magnesium ions. By immersing a wick and/or diffuser with $Mg^{2+}$-Erio T, the wick and/or the diffuser turn blue. If the fragrance preparation comprises a complexant that dissolves Mg out of the colorant complex, e.g. EDTA or crown ethers, then the wick and/or the diffuser turn red as soon as the fragrance preparation containing the complexant diffuses in. Of course, it is also possible for ERIO T to color the wick and/or diffuser red, and $Mg^{2+}$ from the fragrance preparation on contacting the wick and/or the diffuser turns them blue.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

We claim:

1. A fragrance-dispensing system comprising:
    a. at least one diffuser having a surface in contact with the surrounding air and having at least two groups of lamellae that differ from each other;
    b. a color change agent present in or on at least a section of said diffuser;
    c. a wick having a surface area at least partly exposed to said surrounding air, said wick in contact with said diffuser;
    d. a container for receiving said wick; and
    e. a fragrance preparation in said container and in contact with said wick, said preparation comprising at least one substance capable of reacting with said color change agent,
        wherein (i) said fragrance preparation is transported by means of capillary action against the force of gravity from said container through said wick to said diffuser; (ii) said surface of said diffuser in contact with said surrounding air is greater than said surface of said wick exposed to said surrounding air; (iii) contact of said substance with said color change agent causes a color change to, and/or in, said section of said diffuser; wherein a first color change agent is disposed in a first group of lamellae and a second color change agent is disposed in a second group of lamellae, said first and second color change agents having different compositions.

2. The system according to claim 1, wherein said first color change agent and said second color change agent show a color change with the same or different substances present in the fragrance preparation.

3. The system according to claim 1, wherein said wick and said diffuser comprise a synthetic material or fibrous material of vegetal origin.

4. The system according to claim 1, wherein said wick and said diffuser comprise a cellulosic material.

5. The system according to claim 1, wherein said diffuser comprises an essentially circular base when viewed from the top.

6. The system according to claim 1, and wherein the ratio of the surface of the diffuser in contact with the surrounding air and the surface of the wick in contact with the surrounding air is between 1000:1 and 1.25:1.

7. The system according to claim 1, wherein said ratio is between 125:1 and 2.5:1.

8. The system according to claim 1, wherein the number of the lamellae is at least 6.

9. The system according to claim 1, wherein the number of said lamellae is at least 100.

10. The system according to claim 8, wherein the lamellae each have a surface consisting of upper and lower sides of a lamella, said surface having area from 0.5-100 $cm^2$.

11. The system according to claim 10, wherein said surface of a lamella is from 2-50 $cm^2$.

12. The system according to claim 1, wherein the lamellae are arranged helically or whorled on the wick axis.

13. The system according to claim 1, wherein the angle between two neighboring lamellae is between 3°-140°.

14. The system according to claim 13, wherein said angle is between 4°-137.5°.

15. The system according to claim 1, wherein the diffuser has at least one plane of symmetry.

16. The system according to claim 15, wherein said diffuser has at least two planes of symmetry.

17. The system according to claim 16, wherein said diffuser has at least three planes of symmetry.

18. The system according to claim 1, wherein the color change agent comprises a solvatochromic dye.

19. The system according to claim 1, wherein the color change agent is colorless before contact with the said substance that initiates said color change.

20. The system according to claim 1, wherein the wick and diffuser are each provided with color change agents that differ from one another.

\* \* \* \* \*